United States Patent [19]
Brouwer et al.

[11] Patent Number: 6,017,947
[45] Date of Patent: Jan. 25, 2000

[54] HETEROCYCLIC CARBODITHIOPEROXYIMIDIC COMPOUNDS USEFUL FOR THE INHIBITION OF THE REPLICATION OF HIV

[76] Inventors: Walter Gerhard Brouwer, 15 Hickory St., Guelph, Canada, N1G 2X2; Ewa Maria Osika, 188 Arrowhead Crescent, Kitchener, Canada, N2P 1B9

[21] Appl. No.: 09/399,283

[22] Filed: Sep. 17, 1999

[51] Int. Cl.⁷ .......................... A61K 31/34; A61K 31/38; C07D 307/68; C07D 333/38
[52] U.S. Cl. ................. 514/438; 514/231.3; 514/326; 514/471; 544/146; 544/152; 544/316; 544/333; 546/212; 546/214; 546/280.4; 546/283.4; 549/59; 549/60; 549/75; 549/76; 549/472; 549/491; 549/496
[58] Field of Search .................... 549/59, 60, 75, 549/76, 472, 491, 496; 544/146, 152, 316, 333; 546/212, 214, 280.4, 283.4; 514/231.3, 326, 438, 471

[56] References Cited

U.S. PATENT DOCUMENTS 5,696,151  12/1997  Brouwer et al. .................. 514/448

*Primary Examiner*—Bernard Dentz
*Attorney, Agent, or Firm*—Daniel Reitenbach

[57] ABSTRACT

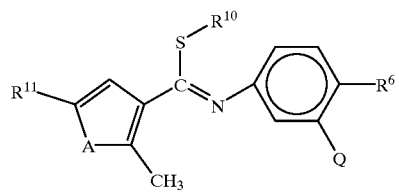

(I)

wherein

A is oxygen or sulphur;

$R^6$ is H, halogen, alkyl, alkoxy, alkylthio, cyano, or nitro;

$R^{10}$ is phenylthio, dialkylamino, alkylthio, alkoxycarbonyl, N-morpholinyl, or N-piperidinyl;

$R^{11}$ is hydrogen or alkyl;

Q is alkoxy, alkenyloxy, alkynyloxy, alkylthio, alkenylthio, alkynylthio, alkoxycarbonyl, alkoxyiminomethyl, or Y—Ar;

Y is —$CH_2O$—, —$OCH_2$—, —$CH_2S$—, or —$CH_2SO_2$—;

Ar is a substituted or unsubstituted phenyl or aromatic heterocyclic group, useful for the inhibition of the replication of HIV-1, in vitro and in vivo.

28 Claims, No Drawings

HETEROCYCLIC CARBODITHIOPEROXYIMIDIC COMPOUNDS USEFUL FOR THE INHIBITION OF THE REPLICATION OF HIV

FIELD OF THE INVENTION

This invention relates to heterocyclic carbodithioperoxyimidic compounds useful for the inhibition of the replication of HIV. This invention also relates to a method for the prevention or treatment of HIV-1 infection in a patient which comprises administering to the patient an effective amount of the heterocyclic carbodithioperoxyimidic compounds.

BACKGROUND OF THE INVENTION

Various compounds have been described as inhibitors of human immunodeficiency virus type 1 (HIV-1) in vitro and are targeted at the virus-encoded reverse transcriptase (RT), e.g., nevirapine, pyridinone, TIBO, BHAP, TSAO, and quinoxaline. U.S. Pat. Nos. 5,268,389 and 5,693,827 describe certain compounds useful for inhibiting the replication of HIV. The selectivity of these compounds for HIV-1 is due to a highly specific interaction with HIV-1 RT.

The rapid emergence of HIV-1 strains resistant to several HIV-1 specific RT inhibitors in cell culture and in AIDS patients has caused concern for further development of these inhibitors in the clinic. For example, HIV-1 strains containing the 100 Leu→Ile mutation in their RT are resistant to TIBO R82913 and R82150. HIV-1 strains containing the 138 Glu→Lys mutation in their RT are resistant to TSAO derivatives. The 181 Tyr→Cys mutation in the RT of HIV-1 strains renders the mutant viruses resistant to nevirapine and pyridinone. See, e.g. Balzarini et al, J. Virology 67(9): 5353–5359 (1993) ("Balzarini II") and Balzarini et al. Virology 192: 246–253 (1993) ("Balzarini II"). Attempts have been made to combine various HIV-1 RT inhibitors to eliminate virus resistance. See, e.g., Balzarini I.

U.S. Pat. No. 5,696,151 describes certain methylfuranyl- and methylthienyl-pentenylether derivatives useful against HIV-1 and HIV-1 reverse transcriptase mutants.

It is the purpose of this invention to provide new compounds which by themselves, can inhibit or suppress the emergence of wild-type HIV-1 and HIV-1 RT mutant strains. It is also the purpose of this invention to provide a method of preventing or treating HIV-1 infections by administration of such compounds.

SUMMARY OF THE INVENTION

This invention relates to a compound of the formula

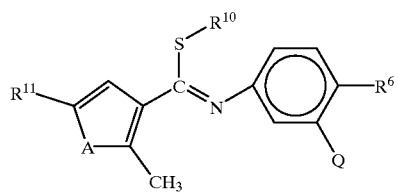

(I)

wherein

A is oxygen or sulphur;

$R^6$ is H, halogen, $C_1$–$C_4$ alkyl, $C_1$–$C_4$ alkoxy, $C_1$–$C_4$ alkylthio, cyano, or nitro;

$R^{10}$ is phenylthio, di ($C_1$–$C_4$ alkyl)amino, $C_1$–$C_4$ alkylthio, ($C_1$–$C_4$ alkoxy)carbonyl, N-morpholinyl, or N-piperidinyl;

$R^{11}$ is hydrogen or $C_1$–$C_4$ alkyl;

Q is $C_1$–$C_8$ alkoxy, $C_1$–$C_8$ alkenyloxy, $C_1$–$C_8$ alkynyloxy, $C_1$–$C_8$ alkylthio, $C_1$–$C_8$ alkenylthio, $C_1$–$C_8$ alkynylthio, ($C_1$–$C_8$ alkoxy)carbonyl, ($C_1$–$C_4$ alkoxy) iminomethyl, or Y—Ar;

Y is —$CH_2O$—, —$OCH_2$—, —$CH_2S$—, or —$CH_2SO_2$—;

Ar is:

(A) an aromatic group of the structure

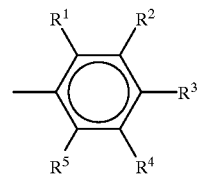

(A)

wherein $R^1$ to $R^5$ are each independently:

(i) hydrogen, halogen, $C_1$–$C_6$ alkyl, $C_1$–$C_4$ alkoxy, $C_1$–$C_4$ alkylthio, cyano, nitro, hydroxy, acetyloxy, benzoyloxy, amino, acetamido, phenyl, acetyloxymethyl, hydroxymethyl, trihalomethyl, carboxy, ($C_1$–$C_4$ alkoxy)carbonyl, formyl, ($C_1$–$C_4$ alkyl)carbonyl, benzoyl, or phenylmethyl; or (ii) a group of the formula

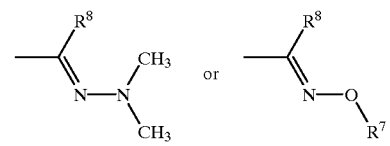

wherein $R^7$ is H, $C_1$–$C_4$ alkyl, $C_1$–$C_4$ haloalkyl, aminocarbonylmethyl, ($C_1$–$C_6$ alkoxy)carbonylmethyl, cyanomethyl, or arylmethyl and $R^8$ is hydrogen or methyl;

or (B) a group of the formula

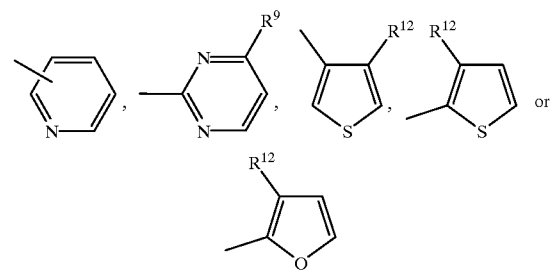

wherein
$R^9$ is $C_1$–$C_4$ alkyl, or $C_1$–$C_4$ fluoroalkyl, and
$R^{12}$ is H, chlorine, bromine, $C_1$–$C_4$ alkyl or ($C_1$–$C_4$ alkoxy)carbonyl.

The compounds of this invention are useful for the inhibition of the replication of Human Immunodeficiency Virus-1 (HIV-1), in vitro and in vivo. The compounds are useful in the therapeutic or prophylactic treatment of diseases caused by HIV-1 thereof, such as acquired immune deficiency syndrome (AIDS).

This invention additionally relates to a pharmaceutical composition comprising a therapeutically effective amount of the compound of formula I and a pharmaceutically acceptable carrier.

This invention also relates to a method of treating HIV-1 infection in an afflicted host which comprises administering to the host a therapeutically effective amount of the compound of formula I.

DESCRIPTION OF THE INVENTION

Preferred compounds of this invention are those compounds of formula I wherein:

A is oxygen or sulfur;

$R^6$ is hydrogen, halogen, $C_1$–$C_4$ alkyl, $C_1$–$C_4$ alkoxy, $C_1$–$C_4$ alkylthio, cyano, or nitro;

$R^{10}$ is phenylthio, di($C_1$–$C_4$ alkyl)amino, $C_1$–$C_4$ alkylthio, ($C_1$–$C_4$ alkoxy)carbonyl, N-morpholinyl, or N-piperidinyl;

$R^{11}$ is hydrogen or $C_1$–$C_4$ alkyl;

Q is $C_1$–$C_8$ alkoxy, $C_1$–$C_8$ alkenyloxy, $C_1$–$C_8$ alkynyloxy, $C_1$–$C_8$ alkylthio, $C_1$–$C_8$ alkenylthio, $C_1$–$C_8$ alkynylthio, ($C_1$–$C_8$ alkoxy)carbonyl, ($C_1$–$C_4$ alkoxy) iminomethyl, or Y—Ar;

Y is —CH$_2$O—, —OCH$_2$—, or —CH$_2$S—;

Ar is an aromatic group of the structure

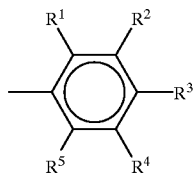

(A)

wherein $R^1$ to $R^5$ are each independently hydrogen, halogen, $C_1$–$C_6$ alkyl, $C_1$–$C_6$ alkoxy, trihalomethyl, cyano, nitro, or trihalomethoxy.

More preferred are those compounds of formula I wherein

A is oxygen or sulfur;

$R^6$ is halogen or $C_1$–$C_4$ alkyl;

$R^{10}$ is phenylthio, $C_1$–$C_4$ alkylthio, ($C_1$–$C_4$ alkoxy) carbonyl, N-morpholinyl, or N-piperidinyl;

$R^{11}$ is hydrogen or methyl; and

Q is $C_1$–$C_4$ alkoxy, $C_1$–$C_4$ alkenyloxy, $C_1$–$C_4$ alkynyloxy, $C_1$–$C_4$ alkylthio, $C_1$–$C_4$ alkenylthio, $C_1$–$C_4$ alkynylthio, ($C_1$–C, alkoxy)carbonyl, or ($C_1$–$C_4$ alkoxy)iminomethyl.

Method of Synthesis

The compounds of this invention can be prepared according to the following scheme (A, Q, $R^6$, $R^{10}$ and $R^{11}$ are as defined above):

(1) Acid chloride formation

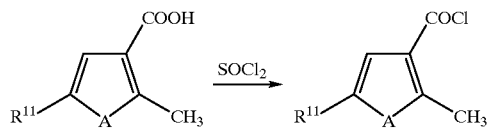

(2) Substituted protected hydroxymethyl aniline preparation

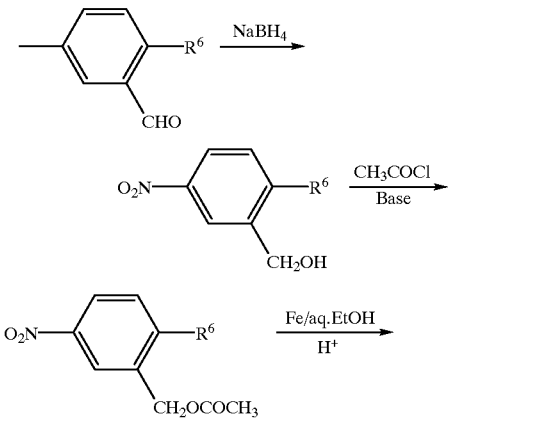

(3) Amide Formation

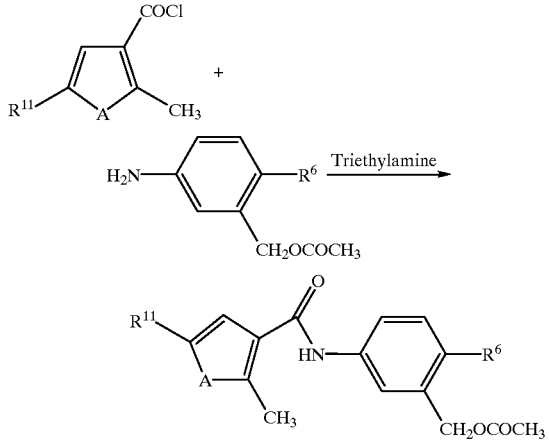

(4) Deprotection bromination

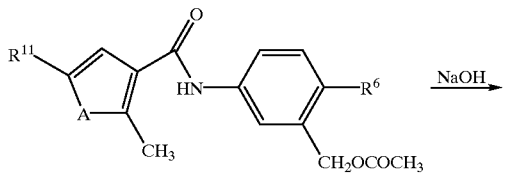

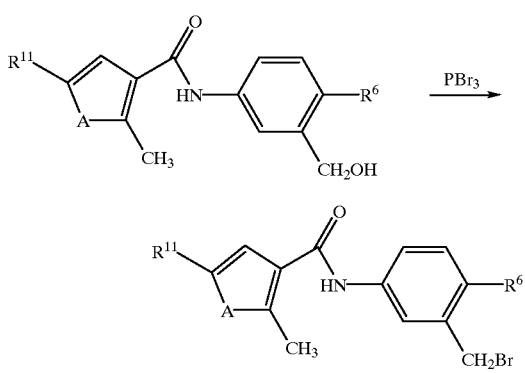

(5) Arylation

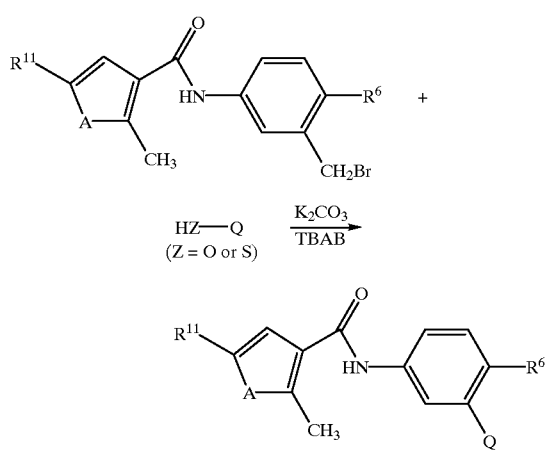

(6) Thionylation

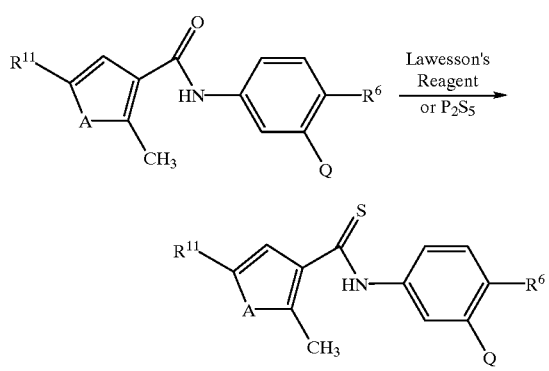

(7) Sulfenylation

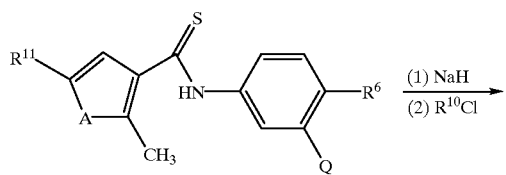

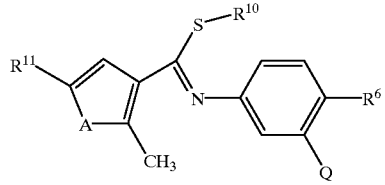

The compounds of the present invention can be administered orally, parenterally, sublingually, by inhalation spray, rectally, or topically in dosage unit formulations containing conventional non-toxic pharmaceutically acceptable carriers, adjuvants, and vehicles. Pharmaceutically acceptable carriers, adjuvants and vehicles useful in the composition of this invention can be found in standard pharmaceutical texts such as, e.g., *Remington's Pharmaceutical Sciences*, 16th Edition, Mack Publishing Company, Easton, Pa. (1980).

The therapeutically effective amount of the compounds of this invention that can be combined with the pharmaceutically acceptable carrier to produce a single dosage form will vary depending upon the age and condition of the host treated and the particular mode of administration. In general, the compounds of this invention are most desirably administered at a concentration level that will generally afford anti-virally effective results without causing any harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated.

The following examples are provided to illustrate the present invention.

EXAMPLES

Materials and Methods

A. Preparation of N-[4-chloro-3-(3-methylbutoxy)-phenyl]-2-methyl-3-thiophenecarbodithioperoxyimidic acid methyl ester (Compound No. 1)

N-[4-chloro(3-methyl-2-butenyloxy)phenyl]-2-methyl-3-thiophenecarbothioamide (1.12 g) in THF (10 mL) was added to a suspension of sodium hydride (60%, 0.14 g)in THF(12 mL)and the resultant reaction mixture was cooled to −78° C. To the cooled reaction mixture was added dropwise, a solution of methanesulphenyl chloride (0.35 g) in THF (10 mL). The reaction mixture was then allowed to come to room temperature and then left overnight at room temperature. An equal volume of water was added to the reaction mixture, the reaction mixture was extracted with ether, and the organic layer was dried over magnisium sulphate and reduced to an oil (1.2 g). The oil was then purified by column chromatography (ethyl acetate (10% ) in hexane on silica gel) to produce 0.6 g of N-[4-chloro-3-(3-methylbutoxy) phenyl]-2-methyl-3-thiophenecarbodithio-peroxyimidic acid methyl ester as an oil, whose NMR spectrum was consistent with the desired structure.

B. Preparation of N-[4-chloro-3-[(3-methyl-2-butenyl)oxy]-phenyl]-2-methyl-3-furancarbothioperoxyimidic acid methyl ester (Compound No. 4)

A solution of N-[4-chloro-3-[(3-methyl-2-butenyl)-oxy] phenyl]-2-methyl-3-furancarbothioamide (0.98 g) in THF (12 mL) was added to a suspension of 60% sodium hydride (0.12 g) in THF (15 mL). The resultant reaction mixture cooled to −78° C. and a solution of methanesulphenyl chloride (0.32 g) in THF (10 mL), was added dropwise. The reaction mixture was kept at −78° C. for 90 minutes. Water (25 mL) and ether (25 mL) were then added to the reaction mixture, followed by aqueous sodium bicarbonate (20 mL). The resultant organic layer was then separated and washed with water, dried over magnesium sulphate and reduced to an oil (1.1 g) which was substantially pure. Further chromatography (10% ethyl acetate in hexane on silica gel) gave 0.86 g of N-[4-chloro-3-[(3-methyl-2-butenyl)oxy]-phenyl]-2-methyl-3-furancarbothioperoxyimidic acid methyl ester as an oil whose NMR spectrum was consistent with the named structure.

C. Preparation of N-[4-chloro-3-[[(1-methylethoxy)imino]-methyl]iphenyl]-2-methyl-3-furancarbodithioperoxyimidic acid methyl ester (Compound No. 5)

A solution of N-[4-chloro-3-[[(1-methylethoxy)imino]-methyl]phenyl-2-methyl-3-furancarbothioamide (1.68 g) in THF (20 ML)was added dropwise to a suspension of 60% of NaH (previously washed with ligroin)(0.21 g) in THF (20 mL) at below 15° C. The resultant reaction mixture was then stirred for 30 minutes and then cooled to −78° C. Methanesulphenyl chloride (0.57 g) was then added over 30 minutes and the resultant reaction mixture was stirred at −78° C. for 90 minutes until thin layer chromatography (TLC) showed the disappearance of starting material. Ether (20 mL) and aqueous sodium bicarbonate solution (50 mL) were then added to the reaction mixture. The resultant organic layer was separated, washed with water, dried over magnesium sulfate, and evaporated to produce an oil (2 g) which was purified repeatedly by column chromatography (10% ethyl acetate in hexane on silica gel) to give 1.2 g of N-[4-chloro-3-[[(1-methylethoxy)imino]-methyl]phenyl]-2-methyl-3-furancarbodithioperoxyimidic acid methyl ester as a yellow oil whose NMR spectrum was consistent with the named structure.

D. Preparation of N-[4-chloro-3-[2-chlorophenoxy)-methyl]phenyl]-2-methyl-3-furancarbodithioperoxyimidic acid methyl ester (Compound No. 7)

A solution of N-[4-chloro-3-[(2-chlorophenoxy)-methyl]-2-methyl-3-furancarbothioamide (1.8 g) in THF (20 mL) was added to 60% NaH (0.21 g, previously washed with ligroin) suspended in THF, keeping the temperature below 10° C. The resultant reaction mixture was then stirred for 1 hour and then chilled to −78° C. with dry ice and acetone. A solution of methanesulphenyl chloride (0.61 g) in THF (5 mL) was then added to the reaction mixture. The reaction mixture was then stirred at −78° for 1 hour until thin layer chromatography (TLC) showed the disappearance of starting material. Ether (20 mL) and aqueous sodium bicarbonate solution (20 mL) were then added to the reaction mixture. The resultant organic layer was separated, washed with water, dried over sodium sulfate, and evaporated to produce an oil (2.1 g) which was purified twice by column chromatography (10% ethyl acetate in hexane on silica gel) to produce 0.58 g of N-[4-chloro-3-[2-chlorophenoxy)-methyl]phenyl]-2-methyl-3-furancarbodithioperoxyimidic acid methyl ester as an oil whose NMR spectrum was consistent with the desired structure.

E. Preparation of N-[4-chloro-3-[(3-methyl-2-butenyl)oxy]phenyl]-2,5-dimethyl-3-furancarbodithioperoxyimidic acid methyl ester (Compound No. 9)

A solution of N-[4-chloro-3-methyl-2-butenyl)oxy]-phenyl-2,5-dimethyl-3-furancarbothioamide (1 g) in THF (5 mL) was added to a suspension of sodium hydride (60%), (previously washed in ligroin)(0.14 g) in THF (10 mL). When effervescence ceased the reaction mixture was cooled to −78° C. and a solution of methanesulphenyl chloride (0.34 g) in THF (6 g) was added dropwise. After 15 minutes ether (30 mL) was added, and the reaction mixture poured into saturated aqueous sodium biocarbonate solution (40 mL). A white inorganic precipitate was removed by filtration, the organic layer separated, and the aqueous layer washed with ether. The combined ether washing and organic layer was dried over magnesium sulphate and reduced in volume to give a yellow oil (1.23 g). Purification by column chromatography on silica gel (10% ethyl acetate in hexane) gave 0.75 g of N-[4-chloro-3-[(3-methyl-2-butenyl)oxy] phenyl]-2,5-dimethyl-3-furan-carbodithioperoxyimidic acid methyl ester as an oil whose NMR spectrum was consistent with the named compound.

F. Preparation of N-[4-chloro-3-methyl-2-butenyl)-oxyliphenyl]-2-methyl-3-furancarbodithioperoxvimidic acid phenyl ester (Compound No. 10)

A solution of N-[4-chloro-3-methyl-2-butenyl)oxy]-phenyl]-2-methyl-3-furancarbothioamide (1.04 g) in THF (10 mL) was added dropwise to a suspension of 60% sodium hydride (previously washed in lifroin)(0.12 g) at room temperature. When the solution became clear more sodium hydride was added until effervescence ceased. The resultant reaction mixture was cooled to −78° C. Phenylsulphenyl chloride (0.43 g) in dry THF (3 mL) was then added dropwise to the reaction mixture. The reaction mixture was then left 30 minutes at −78° C. Ether (25 mL) was then added and the solution. The resultant organic layer was then washed with water (2×25 mL), dried over sodium sulphate, and reduced in volume to yield a yellow oil (1.35 g) which was purified on a silica-gel column with 10% ethyl acetate in hexane, to produce 0.56 g of N-[4-chloro-3-methyl-2-butenyl)oxy]phenyl]-2-methyl-3-furancarbodithioperoxyimidic acid phenyl ester as an oil whose NMR spectrum was consistent with the named compound.

G. Preparation of 4-[[[[4-chloro-3-[(3-methyl-2-butenyl)oxy]pohenyl]iminol][2-methyl-3-furanyl]methyl]-thio]morpholine (Compound No. 11)

A solution of N-[4-chloro-3-[(3-methyl-2-butenyl)-oxy] phenyl]-2-methyl-3-furancarbothioamide (3.4 g) in THF (40 mL) was added to a suspension of sodium hydride (60%, 0.5 g) in THF. To the resultant reaction mixture was added 4-chloromorpholine prepared from morpholine (10 mL) and sodium hypochlorite (350 mL). After 15 minutes the reaction mixture was poured into an aqueous solution of sodium sulphite (12 g) in water (350 mL) and extracted with ether. The ether extract was washed with water and dried. Chromatography of the reduced extract gave 2 g of 4-[[[[4-chloro-3-[(3-methyl-2-butenyl)oxy]phenyl]-imino][2-methyl-3-furanyl]methyl]thio]morpholine as an oil whose NMR was consistent with the named structure.

H. Preparation of N-[4-chloro-3-[(3-methyl-2-butenyl)oxy] iphenyl]-2-methyl-3-furancarboximidothioic acid S-ethoxycarbonyl ester (Compound 12)

A solution of N-[4-chloro-3-[(3methyl-2-butenyl)oxy]-phenyl]-2-methyl-3-furancarabothioamide in THF (5 mL) was added dropwise to a suspension of 60% sodium hydride (0.13 g) in THF (12 mL) and stirred for 1 hour, cooled to 0° C., and ethyl chloroformate (0.13 g) in THF (5 mL) added dropwise. The resultant reaction mixture was stirred at room temperature overnight. Water was then added and the resultant solution was extracted with ether. The ether extract was washed with aqueous sodium bicarbonate solution and brine, dried over magnesium sulfate and evaporated to give 1.3 g of an orange oil which solidified when covered by ligroin. Purified by column chromatography of the oil on silica gel with dichloromethane produced 0.38 g of N-[4-chloro-3-[(3-methyl-2-butenyl)oxy]phenyl]-2-methyl-3-furancarboximidothioic acid S-ethoxycarbonyl ester as an orange solid whose NMR spectrum was consistent with the named structure.

The other compounds listed below in Table 1 were prepared in similar manner.

TABLE 1

| Cmpd | A | R[11] | R[10] | Q |
|---|---|---|---|---|
| 1 | S | H | $SCH_3$ | 3-methylbutoxy |
| 2 | S | H | $SCH_3$ | (2,4-dimethyl-3-pentyloxy)carbonyl |
| 3 | O | H | $SCH_3$ | [(1,1-dimethylethoxy)-imino]methyl |
| 4 | O | H | $SCH_3$ | (3-methyl-2-butenyl)oxy |
| 5 | O | H | $SCH_3$ | [(1-methylethoxy)imino]-methyl |
| 6 | O | H | $SCH_3$ | 3-methylbutoxy |
| 7 | O | H | $SCH_3$ | (2-chlorophenoxy)methyl |
| 8 | O | H | $SC_6H_5$ | [(1,1-dimethylethoxy)-imino]methyl |
| 9 | O | $CH_3$ | $SCH_3$ | (3-methyl-2-butenyl)oxy |
| 10 | O | H | $SC_6H_5$ | (3-methyl-2-butenyl)oxy |
| 11 | O | H | 4-morpholinyl | (3-methyl-2-butenyl)oxy |
| 12 | O | H | $CO_2C_2H_5$ | (3-methyl-2-butenyl)oxy |

Cells and Viruses CEM cells were obtained from the American Tissue Cell Culture Collection (Rockville, Md.). HIV-1 (III$_B$) was originally obtained from the culture supernatant of persistently HIV-1-infected H9 cells and was provided by R. C. Gallo and M. Popovic (National Cancer Institute, National Institutes of Health, Bethesda, Md.).

The selection and characterization of the HIV-1 RT mutant strains were done as follows: HIV-1/100-Ile ("100-Ile") was selected for resistance against TIBO R82150 as described in Balzarini et al, Virology 192: 246–253 (1993); HIV-1/103-Asn ("103-Asn") was selected for resistance against TIBO R82913 as described in Balzarini et al, Virology 192: 246–253 (1993); HIV-1/106-Ala ("106-Ala") was selected for resistance against nevirapine as described in Balzarini et al, J. Virol. 67: 5353–5359 (1993); HIV-1/Lys-138 ("ys-138") was selected for resistance against TSAO-m$^3$T as described in Balzarini et al, Virology 192: 246–253 (1993) and Balzarini et al, Proc. Nat. Acad. Sci. USA 90: 6952–6956 (1993); HIV-1/181-Cys ("181-Cys") was selected for resistance against pyridinone L-697,661 as described in Balzarini et al, Virology 192: 246–253 (1993); and HIV-1/188-His ("188-His") was selected for resistance against HEPT as described in Balzarini et al, Mol. Pharmocol. 44: 694–701 (1993). 188-His was then further converted to HIV-1/188-Leu("188-Leu") upon further passage in cell culture in the absence of the HEPT. HIV-1/101-Glu ("101-Glu") and HIV-1/190-Glu ("190-Glu") were selected for resistance against the thiocarboxanilide derivative designated as UC38 as described in Balzarini et al, Antiviral Research 27: 219–236 (1995). HIV-1/184-Ile ("184-Ile") was selected for resistance against the combination of 3TC and TSAO-m$^3$T as described in Balzarini et al, Molecular Pharm. 49: 882–890 (1996). HIV-1/184-Val ("184-Val") was selected for resistance against 3TC as described in Balzarini et al, Molecular Pharm. 49: 882–890 (1996).

Antiviral Activity of the Test Compounds in Cell Cultures

CEM cells were suspended at ≈300,000 cells per ml of culture medium and infected with approximately 100 $CCID_{50}$ ($CCID_{50}$ being the 50% cell culture infective dose) of HIV-1(III$_B$) (designated as "WT" in Table 3) or one of the HIV-1 RT mutant strains described above. Then 100 μl of the infected cell suspensions was added to 200 μl microtiter plate wells containing 100 μl of appropriate serial (5-fold) dilutions of the test compounds. The inhibitiory effect of the test compounds on HIV-1 induced syncytium formation in CEM cells was examined microscopically on day 4 post infection. The 50% effective concentration ($EC_{50}$) was defined as the test compound concentration that inhibits syncytium formation in the HIV-1–infected cell cultures by 50%.

TABLE 2

Activity Against HIV-1(III$_B$)

| Compound No. | $EC_{50}$ (mmol/ml) |
|---|---|
| 1 | $1.04 \times 10^{-7}$; $1.86 \times 10^{-7}$; $1.02 \times 10^{-7}$ |
| 2 | $2.2 \times 10^{-7}$; $1.07 \times 10^{-7}$ |
| 3 | $1.28 \times 10^{-7}$; $1.21 \times 10^{-7}$; $1.26 \times 10^{-7}$ |
| 4 | $3.65 \times 10^{-9}$; $1.10 \times 10^{-8}$ |
| 5 | $7.32 \times 10^{-8}$; $4.31 \times 10^{-8}$ |
| 6 | $8.37 \times 10^{-8}$; $8.04 \times 10^{-8}$ |
| 7 | $4.86 \times 10^{-8}$; $5.33 \times 10^{-8}$ |
| 8 | $1.56 \times 10^{-7}$; $8.32 \times 10^{-8}$ |
| 9 | $6.50 \times 10^{-8}$; $6.69 \times 10^{-8}$ |
| 11 | $1.63 \times 10^{-8}$; $1.24 \times 10^{-8}$ |

TABLE 3

Activity Against HIV-1(III$_B$) and HIV-1 RT Mutants

| | $EC_{50}$ (μg/ml) | | | | | | | | | | | |
|---|---|---|---|---|---|---|---|---|---|---|---|---|
| No. | WT | 100-Ile | 101-Glu | 103-Asn | 106-Ala | 138-Lys | 181-Cys | 184-Ile | 184-Val | 188-His | 188-Leu | 190-Glu |
| 3 | 0.018 | 0.47 | 0.14 | 1.33 | 0.18 | 0.1 | 0.1 | 0.03 | 0.12 | 0.8 | 1.35 | >2 |
| 4 | 0.0018 | 0.053 | 0.027 | 0.15 | 0.018 | 0.008 | 0.08 | 0.0032 | 0.0015 | 0.85 | 0.58 | >2 |
| 5 | 0.0075 | 0.25 | 0.13 | 0.85 | 0.1 | 0.1 | 0.18 | 0.013 | 0.0075 | 0.7 | 0.95 | >2 |
| 6 | 0.012 | 0.25 | 0.13 | 0.65 | 0.13 | 0.15 | 0.29 | 0.02 | 0.008 | ≧2 | >2 | >2 |
| 7 | 0.0075 | 0.93 | 0.34 | ≧2 | 0.55 | 0.13 | 0.47 | 0.02 | 0.009 | 0.65 | 0.7 | >2 |
| 8 | 0.03 | 0.65 | 0.2 | ≧2 | 0.7 | 0.18 | 0.23 | 0.03 | 0.018 | ≧2 | >2 | >2 |
| 9 | 0.0097 | ≧2 | 0.28 | ≧2 | 0.20 | 0.09 | 0.7 | 0.05 | 0.009 | ≧2 | ≧2 | >2 |

TABLE 3-continued

Activity Against HIV-1(III$_B$) and HIV-1 RT Mutants

| | | | | | | | | | | | | |
|---|---|---|---|---|---|---|---|---|---|---|---|---|
| | | | | | | EC$_{50}$ ($\mu$g/ml) | | | | | | |
| No. | WT | 100-Ile | 101-Glu | 103-Asn | 106-Ala | 138-Lys | 181-Cys | 184-Ile | 184-Val | 188-His | 188-Leu | 190-Glu |
| 10 | 0.05 | 1.5 | 0.2 | ≧2 | 0.5 | 0.23 | ≧2 | 0.09 | 0.053 | ≧2 | >2 | >2 |

What is claimed is:

1. A compound of the formula

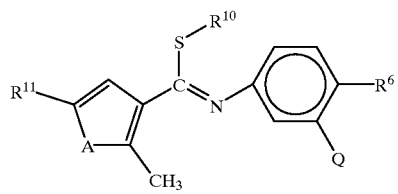

(I)

wherein

A is oxygen or sulphur;

$R^6$ is H, halogen, $C_1$–$C_4$ alkyl, $C_1$–$C_4$ alkoxy, $C_1$–$C_4$ alkylthio, cyano, or nitro;

$R^{10}$ is phenylthio, di($C_1$–$C_4$ alkyl)amino, $C_1$–$C_4$ alkylthio, ($C_1$–$C_4$ alkoxy)carbonyl, N-morpholinyl, or N-piperidinyl;

$R^{11}$ is hydrogen or $C_1$–$C_4$ alkyl;

Q is $C_1$–$C_8$ alkoxy, $C_1$–$C_8$ alkenyloxy, $C_1$–$C_8$ alkynyloxy, $C_1$–$C_8$ alkylthio, $C_1$–$C_8$ alkenylthio, $C_1$–$C_8$ alkynylthio, ($C_1$–$C_8$ alkoxy)carbonyl, ($C_1$–$C_4$ alkoxy)iminomethyl, or Y—Ar;

Y is —CH$_2$O—, —OCH$_2$—, —CH$_2$S—, or —CH$_2$SO$_2$—;

Ar is:

(A) an aromatic group of the structure

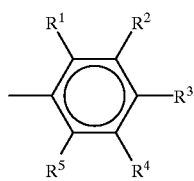

(A)

wherein $R^1$ to $R^5$ are each independently:

(i) hydrogen, halogen, $C_1$–$C_6$ alkyl, $C_1$–$C_4$ alkoxy, $C_1$–$C_4$ alkylthio, cyano, nitro, hydroxy, acetyloxy, benzoyloxy, amino, acetamido, phenyl, acetyloxymethyl, hydroxymethyl, trihalomethyl, carboxy, ($C_1$–$C_4$ alkoxy)carbonyl, formyl, ($C_1$–$C_4$ alkyl)carbonyl, benzoyl, or phenylmethyl; or (ii) a group of the formula

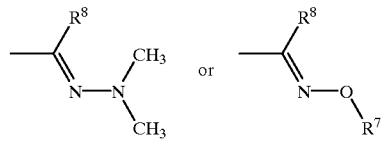

wherein $R^7$ is H, $C_1$–$C_4$ alkyl, $C_1$–$C_4$ haloalkyl, aminocarbonylmethyl, ($C_1$–$C_6$ alkoxy)carbonylmethyl, cyanomethyl, or arylmethyl and $R^8$ is hydrogen or methyl;

or (B) a group of the formula

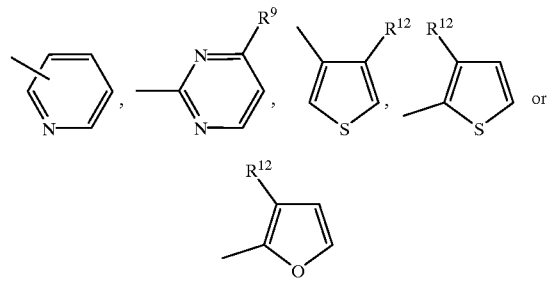

wherein $R^9$ is $C_1$–$C_4$ alkyl, or $C_1$–$C_4$ fluoroalkyl, and $R^{12}$ is H, chlorine, bromine, $C_1$–$C_4$ alkyl or ($C_1$–$C_4$ alkoxy)carbonyl.

2. A compound as recited in claim 1 wherein Q is $C_1$–$C_8$ alkoxy, $C_1$–$C_8$ alkenyloxy, $C_1$–$C_8$ alkynyloxy, $C_1$–$C_8$ alkylthio, $C_1$–$C_8$ alkenylthio, $C_1$–$C_8$ alkynylthio, ($C_1$–$C_8$ alkoxy)carbonyl, or ($C_1$–$C_4$ alkoxy)iminomethyl.

3. A compound as recited in claim 2 wherein Q is $C_1$–$C_4$ alkoxy, $C_1$–$C_4$ alkenyloxy, $C_1$–$C_4$ alkynyloxy, $C_1$–$C_4$ alkylthio, $C_1$–$C_4$ alkenylthio, $C_1$–$C_4$ alkynylthio, ($C_1$–$C_8$ alkoxy)carbonyl, or ($C_1$–$C_4$ alkoxy)iminomethyl.

4. A compound as recited in claim 3 wherein $R^{10}$ is phenylthio, $C_1$–$C_4$ alkylthio, ($C_1$–$C_4$ alkoxy)carbonyl, N-morpholinyl, or N-piperidinyl; and $R^{11}$ is hydrogen or methyl.

5. A compound as recited in claim 1 wherein

Q is Y—Ar;

Y is —CH$_2$O—, —OCH$_2$—, or —CH$_2$S—;

Ar is a group of the structure

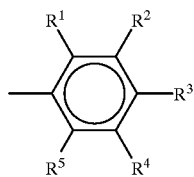
(A)

wherein $R^1$ to $R^5$ are each independently hydrogen, halogen, $C_1$–$C_6$ alkyl, $C_1$–$C_6$ alkoxy, trihalomethyl, cyano, nitro, or trihalomethoxy.

6. A compound as recited in claim 5 wherein
   Y is —CH$_2$O— or —OCH$_2$—;
   Ar is a group of the structure

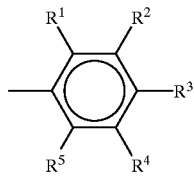
(A)

wherein $R^1$ to $R^5$ are each independently hydrogen, fluoro, chloro, methyl, methoxy, trifluoromethyl, trifluoromethoxy, cyano, or nitro.

7. A compound as recited in claim 6 wherein
   $R^{10}$ is phenylthio, $C_1$–$C_4$ alkylthio, ($C_1$–$C_4$ alkoxy) carbonyl, N-morpholinyl, or N-piperidinyl; and
   $R^{11}$ is hydrogen or methyl.

8. A pharmaceutical composition useful for treating HIV-1 infection in an infected host, which composition comprises a therapeutically effective amount of the compound as recited in claim 1 and a pharmaceutically acceptable carrier.

9. A pharmaceutical composition useful for treating HIV-1 infection in an infected host, which composition comprises a therapeutically effective amount of the compound as recited in claim 2 and a pharmaceutically acceptable carrier.

10. A pharmaceutical composition useful for treating HIV-1 infection in an infected host, which composition comprises a therapeutically effective amount of the compound as recited in claim 3 and a pharmaceutically acceptable carrier.

11. A pharmaceutical composition useful for treating HIV-1 infection in an infected host, which composition comprises a therapeutically effective amount of the compound as recited in claim 4 and a pharmaceutically acceptable carrier.

12. A pharmaceutical composition useful for treating HIV-1 infection in an infected host, which composition comprises a therapeutically effective amount of the compound as recited in claim 5 and a pharmaceutically acceptable carrier.

13. A pharmaceutical composition useful for treating HIV-1 infection in an infected host, which composition comprises a therapeutically effective amount of the compound as recited in claim 6 and a pharmaceutically acceptable carrier.

14. A pharmaceutical composition useful for treating HIV-1 infection in an infected host, which composition comprises a therapeutically effective amount of the compound as recited in claim 7 and a pharmaceutically acceptable carrier.

15. A method of treating HIV-1 infection in an afflicted host which comprises administering to the host a therapeutically effective amount of the compound as recited in claim 1.

16. A method of treating HIV-1 infection in an afflicted host which comprises administering to the host a therapeutically effective amount of the compound as recited in claim 2.

17. A method of treating HIV-1 infection in an afflicted host which comprises administering to the host a therapeutically effective amount of the compound as recited in claim 3.

18. A method of treating HIV-1 infection in an afflicted host which comprises administering to the host a therapeutically effective amount of the compound as recited in claim 4.

19. A method of treating HIV-1 infection in an afflicted host which comprises administering to the host a therapeutically effective amount of the compound as recited in claim 5.

20. A method of treating HIV-1 infection in an afflicted host which comprises administering to the host a therapeutically effective amount of the compound as recited in claim 6.

21. A method of treating HIV-1 infection in an afflicted host which comprises administering to the host a therapeutically effective amount of the compound as recited in claim 7.

22. A method of inhibiting the replication of HIV-1 which comprises contacting the HIV-1 with an effective amount of a compound as recited in claim 1.

23. A method of inhibiting the replication of HIV-1 which comprises contacting the HIV-1 with an effective amount of a compound as recited in claim 2.

24. A method of inhibiting the replication of HIV-1 which comprises contacting the HIV-1 with an effective amount of a compound as recited in claim 3.

25. A method of inhibiting the replication of HIV-1 which comprises contacting the HIV-1 with an effective amount of a compound as recited in claim 4.

26. A method of inhibiting the replication of HIV-1 which comprises contacting the HIV-1 with an effective amount of a compound as recited in claim 5.

27. A method of inhibiting the replication of HIV-1 which comprises contacting the HIV-1 with an effective amount of a compound as recited in claim 6.

28. A method of inhibiting the replication of HIV-1 which comprises contacting the HIV-1 with an effective amount of a compound as recited in claim 7.

* * * * *